United States Patent
Shinar et al.

(10) Patent No.: US 10,028,819 B2
(45) Date of Patent: Jul. 24, 2018

(54) MONOFILAMENT IMPLANTS AND SYSTEMS FOR DELIVERY THEREOF

(71) Applicant: Javelin Medical Ltd., Rehovot (IL)

(72) Inventors: Guy Shinar, Ramat Gan (IL); Ofer Yodfat, Modi'in (IL)

(73) Assignee: Javelin Medical Ltd., Yokneam (IL)

( * ) Notice: Subject to any disclaimer, the term of this patent is extended or adjusted under 35 U.S.C. 154(b) by 291 days.

(21) Appl. No.: 14/802,978

(22) Filed: Jul. 17, 2015

(65) Prior Publication Data

US 2015/0320541 A1 Nov. 12, 2015

Related U.S. Application Data

(63) Continuation of application No. PCT/IL2013/050981, filed on Nov. 27, 2013, and a
(Continued)

(51) Int. Cl.
*A61M 29/00* (2006.01)
*A61F 2/01* (2006.01)
(Continued)

(52) U.S. Cl.
CPC .......... *A61F 2/01* (2013.01); *A61B 17/12031* (2013.01); *A61B 17/12036* (2013.01);
(Continued)

(58) Field of Classification Search
CPC ...... A61F 2/013; A61F 2/01; A61F 2002/016; A61F 2230/0067; A61F 2230/008; A61F 2230/0091; A61F 2002/015
(Continued)

(56) References Cited

U.S. PATENT DOCUMENTS 4,494,531 A 1/1985 Gianturco
4,722,350 A * 2/1988 Armeniades ............. A61B 3/16
600/398
(Continued)

FOREIGN PATENT DOCUMENTS

CN 101404960 A 4/2009
CN 102481436 A 5/2012
(Continued)

OTHER PUBLICATIONS

Search Report for Chinese Application No. 2013800741464; dated Apr. 26, 2016.
(Continued)

*Primary Examiner* — Katherine M Shi
(74) *Attorney, Agent, or Firm* — Cooley LLP

(57) ABSTRACT

Systems, devices and methods are presented for embolic protection. In some embodiments, a device for implantation in a patient's vessel containing a fluid flow is provided which comprises proximal and distal ends, an undeployed, substantially linear state, and a deployed, spring-like (helical) state comprising windings. When the device is deployed, the line segment connecting the proximal and distal ends is approximately perpendicular to the majority of the windings and to the fluid flow. In some embodiments, a delivery device for the monofilament device is provided. The delivery device comprises a needle having a lumen, a sharp distal end, and a pusher slidable within the needle. A method for deploying the monofilament device using the delivery device is provided.

18 Claims, 12 Drawing Sheets

Related U.S. Application Data continuation-in-part of application No. 14/552,890, filed on Nov. 25, 2014, now Pat. No. 9,220,588, which is a continuation of application No. PCT/IB2013/001336, filed on May 30, 2013.

(60) Provisional application No. 61/754,264, filed on Jan. 18, 2013, provisional application No. 61/653,676, filed on May 31, 2012, provisional application No. 61/693,979, filed on Aug. 28, 2012, provisional application No. 61/746,423, filed on Dec. 27, 2012.

(51) Int. Cl.
| | |
|---|---|
| *A61F 2/88* | (2006.01) |
| *A61B 17/34* | (2006.01) |
| *A61B 17/12* | (2006.01) |
| *A61B 17/00* | (2006.01) |
| *A61B 90/00* | (2016.01) |

(52) U.S. Cl.
CPC .. *A61B 17/12109* (2013.01); *A61B 17/12145* (2013.01); *A61B 17/3468* (2013.01); *A61F 2/88* (2013.01); *A61B 90/39* (2016.02); *A61B 2017/00004* (2013.01); *A61B 2017/00398* (2013.01); *A61B 2017/1205* (2013.01); *A61B 2017/12063* (2013.01); *A61F 2002/011* (2013.01); *A61F 2002/016* (2013.01); *A61F 2220/0008* (2013.01); *A61F 2220/0016* (2013.01); *A61F 2230/0071* (2013.01); *A61F 2230/0091* (2013.01); *A61F 2250/0098* (2013.01)

(58) Field of Classification Search
USPC .................. 606/108, 191, 194, 198, 200
See application file for complete search history.

(56) References Cited

U.S. PATENT DOCUMENTS

| | | | |
|---|---|---|---|
| 5,413,586 | A | 5/1995 | Dibie et al. |
| 5,634,942 | A | 6/1997 | Chevillon et al. |
| 5,957,940 | A | 9/1999 | Tanner |
| 6,007,558 | A | 12/1999 | Ravenscroft et al. |
| 6,059,825 | A | 5/2000 | Hobbs |
| 6,152,144 | A | 11/2000 | Lesh et al. |
| 6,344,052 | B1 | 2/2002 | Greenan et al. |
| 6,375,671 | B1 | 4/2002 | Kobayashi et al. |
| 6,395,017 | B1 | 5/2002 | Dwyer et al. |
| 6,673,089 | B1 | 1/2004 | Yassour et al. |
| 6,730,108 | B2 | 5/2004 | Van Tassel et al. |
| 7,128,073 | B1 | 10/2006 | Van Der Burg et al. |
| 7,144,363 | B2 | 12/2006 | Pai |
| 7,306,624 | B2 | 12/2007 | Yodfat et al. |
| 7,572,273 | B2 | 8/2009 | Mazzocchi et al. |
| 7,704,267 | B2 | 4/2010 | Tessmer |
| 8,206,412 | B2 | 6/2012 | Galdonik et al. |
| 8,221,446 | B2 | 7/2012 | Pal et al. |
| 2001/0007946 | A1 | 7/2001 | Lenker et al. |
| 2002/0010481 | A1 | 1/2002 | Jayaraman |
| 2002/0188170 | A1 | 12/2002 | Santamore |
| 2003/0100939 | A1 | 5/2003 | Yodfat et al. |
| 2004/0082962 | A1 | 4/2004 | Demarais et al. |
| 2006/0167489 | A1 | 7/2006 | Satake et al. |
| 2006/0212047 | A1 | 9/2006 | Abbott |
| 2007/0010857 | A1 | 1/2007 | Sugimoto |
| 2007/0066863 | A1 | 3/2007 | Rafiee |
| 2007/0156123 | A1 | 7/2007 | Moll et al. |
| 2008/0108933 | A1* | 5/2008 | Yu ...................... A61F 9/00781 604/8 |
| 2008/0183206 | A1 | 7/2008 | Batiste |
| 2008/0269789 | A1 | 10/2008 | Eli |
| 2009/0054905 | A1 | 2/2009 | Levy |
| 2009/0099591 | A1 | 4/2009 | Nardone |
| 2009/0138066 | A1 | 5/2009 | Leopold et al. |
| 2009/0228020 | A1 | 9/2009 | Wallace et al. |
| 2010/0268204 | A1 | 10/2010 | T1eu et al. |
| 2010/0280522 | A1 | 11/2010 | Barry et al. |
| 2011/0021984 | A1 | 1/2011 | Kirschenman et al. |
| 2011/0022149 | A1 | 1/2011 | Cox et al. |
| 2011/0137394 | A1 | 6/2011 | Lunsford et al. |
| 2012/0165919 | A1 | 6/2012 | Cox et al. |
| 2012/0197379 | A1 | 8/2012 | Laske et al. |
| 2012/0245614 | A1 | 9/2012 | Drasler |
| 2012/0289988 | A1 | 11/2012 | Riina et al. |
| 2012/0316597 | A1 | 12/2012 | Fitz et al. |
| 2014/0004503 | A1 | 1/2014 | Cima |

FOREIGN PATENT DOCUMENTS

| | | |
|---|---|---|
| EP | 0495861 | 7/1992 |
| WO | 9104716 | 4/1991 |
| WO | 1998034546 A2 | 8/1998 |
| WO | 2004098420 A2 | 11/2004 |
| WO | 2006055443 A2 | 5/2006 |
| WO | 2006/084156 A2 | 8/2006 |
| WO | 2008042266 A2 | 4/2008 |
| WO | 2012094251 | 4/2012 |
| WO | 2013179137 A2 | 12/2013 |
| WO | 2014102767 A2 | 7/2014 |
| WO | 2014111911 A1 | 7/2014 |

OTHER PUBLICATIONS

Supplementary European Search Report for European Application No. 13871655.0 dated Oct. 13, 2016.
International Preliminary Report on Patentability for International Application No. PCT/IB2013/001336 dated Dec. 2, 2014.
International Search Report and Written Opinion for International Application No. PCT/IB2013/001336 dated Jan. 24, 2014.
International Search Report for International Application No. PCT/IL13/50979 dated Jun. 23, 2014.
International Search Report for International Application No. PCT/IL13/50981 dated Jun. 23, 2014.

* cited by examiner

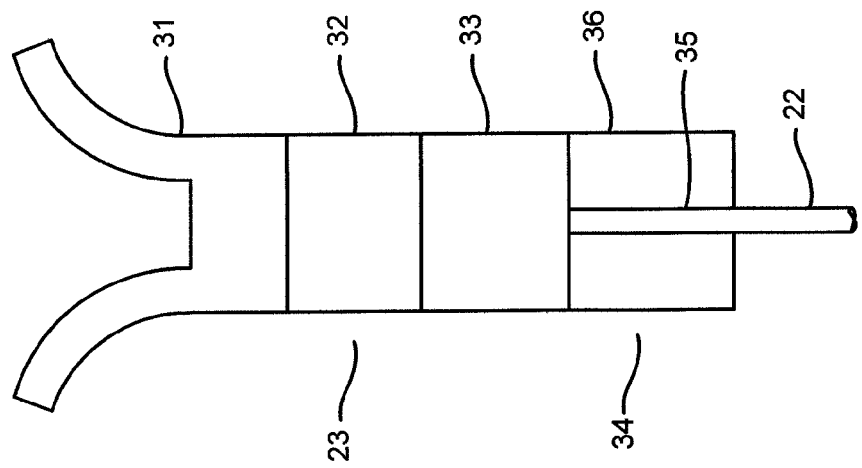
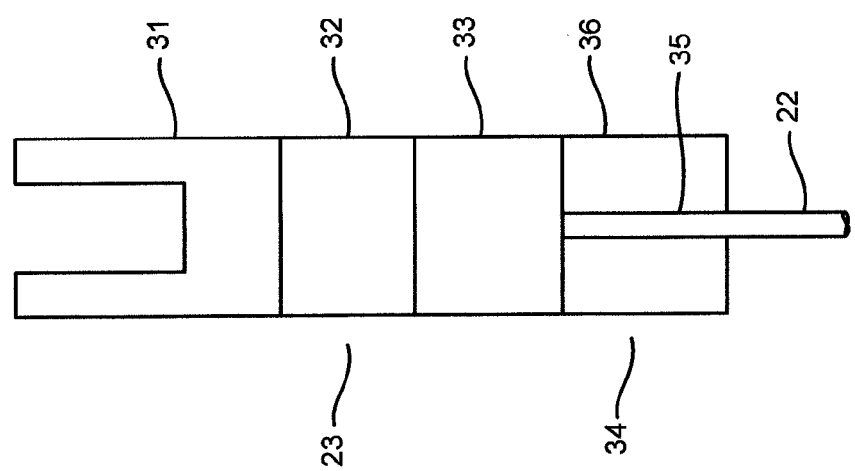
FIG. 3A
FIG. 3B

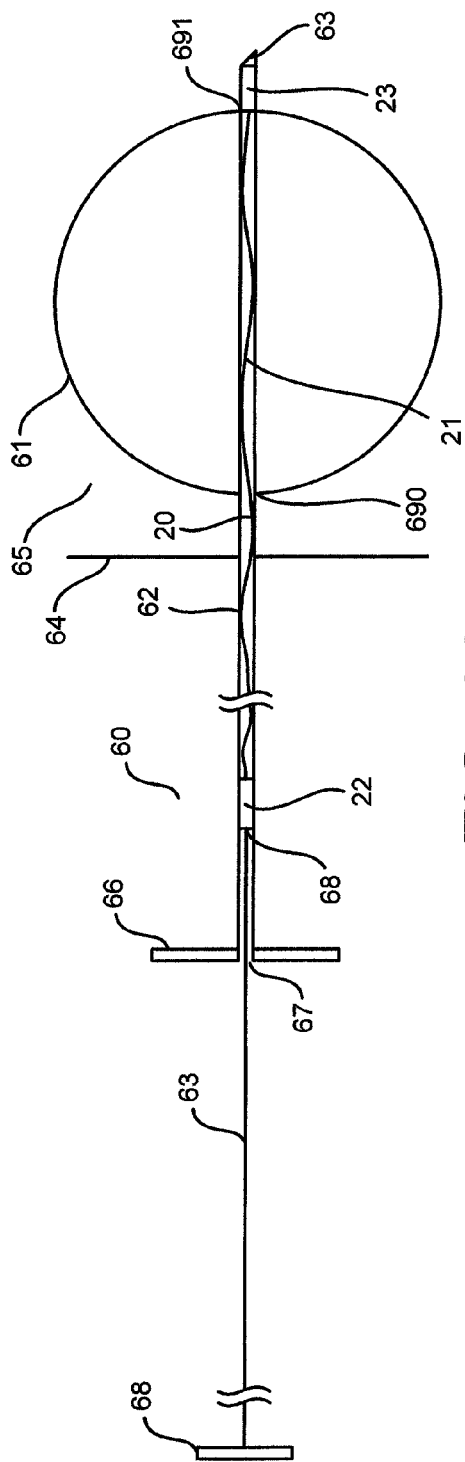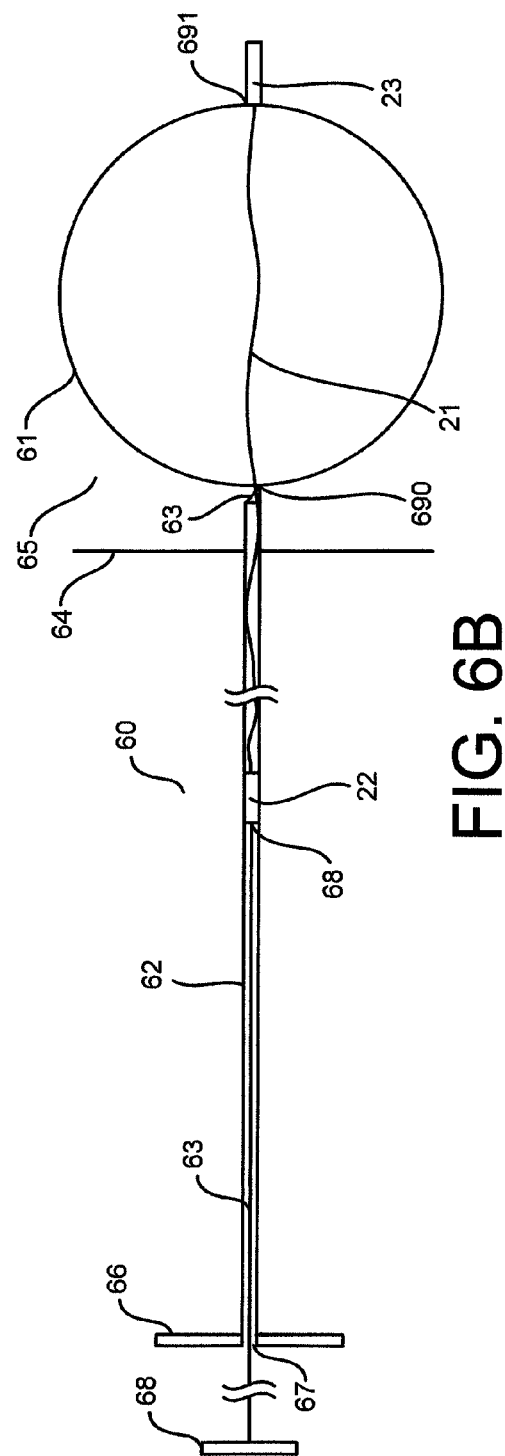

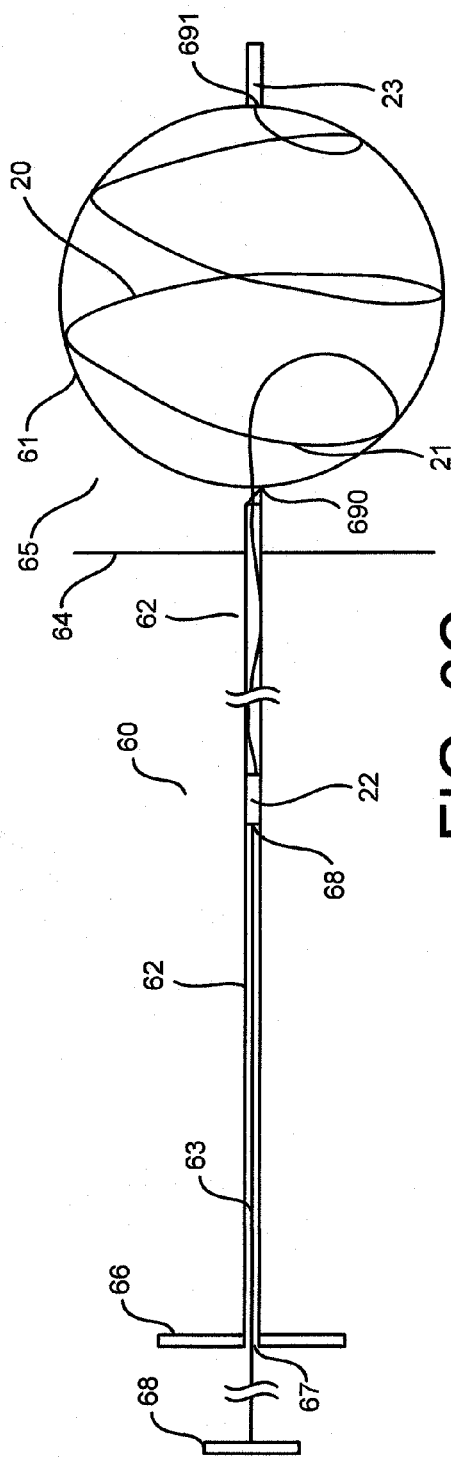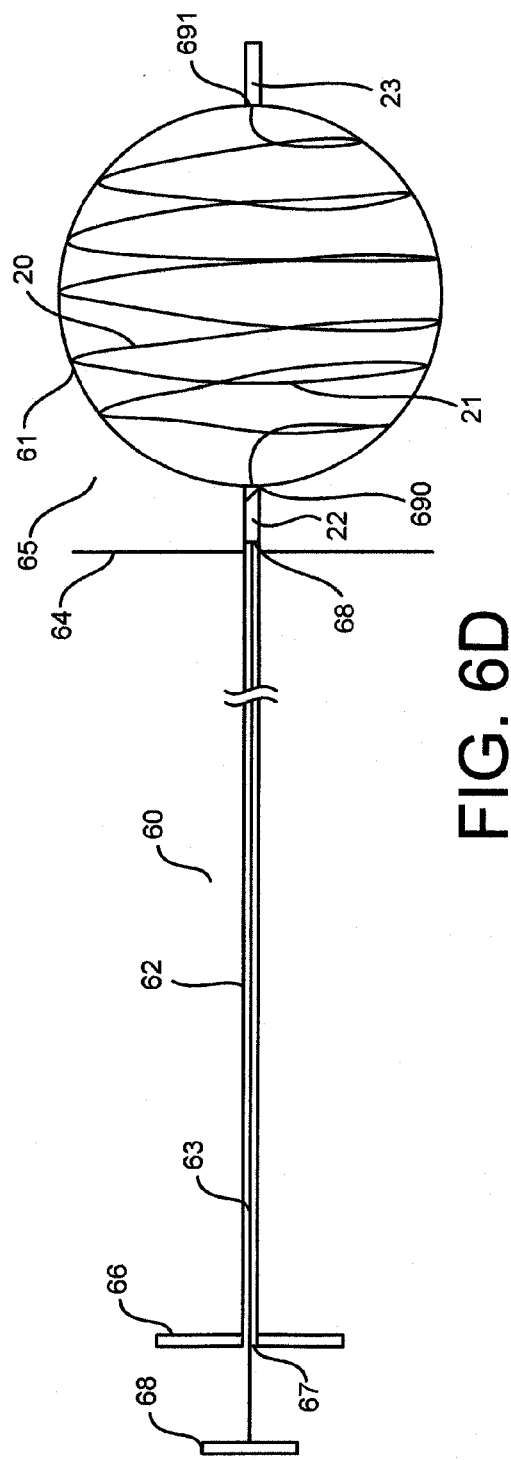
FIG. 6C
FIG. 6D

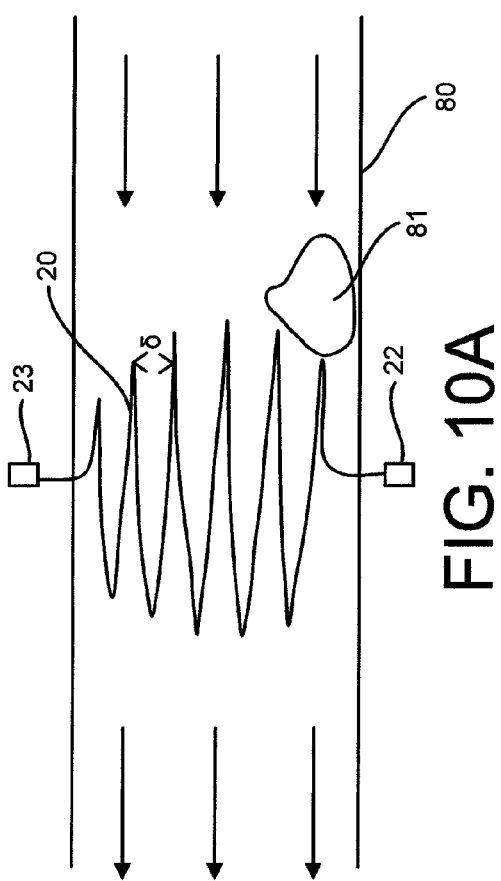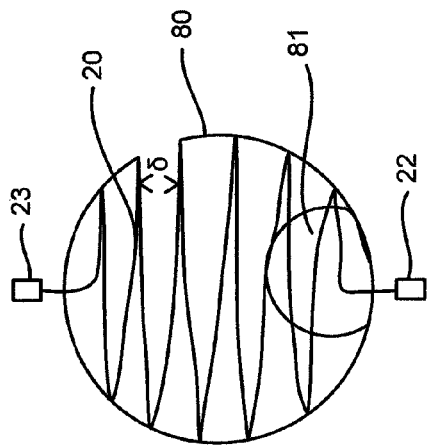
FIG. 10A
FIG. 10B

MONOFILAMENT IMPLANTS AND SYSTEMS FOR DELIVERY THEREOF

RELATED APPLICATIONS

This application is a continuation of and claims priority to International Patent Application No. PCT/IL2013/050981, filed Nov. 27, 2013, and entitled "Monofilament Implants and Systems for Delivery Thereof," which in turn claims priority to U.S. Provisional Patent Application No. 61/754,264, filed Jan. 18, 2013, entitled "Monofilament Implants and Systems for Delivery Thereof."This application also claims priority to pending U.S. patent application Ser. No. 14/552,890, filed Nov. 25, 2014, entitled "Systems, Methods and Devices for Embolic Protection," which in turn is a continuation of and claims priority to International Patent Application No. PCT/IB2013/001336, filed May 30, 2013, and entitled "Systems, Methods and Devices for Embolic Protection," which in turn claims priority to U.S. Provisional Patent Application No. 61/653,676, filed May 31, 2012, and entitled "Apparatus and Methods of Providing Embolic Protection in a Patient," U.S. Provisional Patent Application No. 61/693,979, filed Aug. 28, 2012, and entitled "Apparatus and Method of Providing Embolic Protection in a Body Vessel of a Patient," U.S. Provisional Patent Application No. 61/746,423, filed Dec. 27, 2012, and entitled "Apparatus and Method of Providing Embolic Protection in a Body Vessel of a Patient," and U.S. Provisional Patent Application No. 61/754,264, filed Jan. 18, 2013, and entitled "Monofilament Implants and Systems for Delivery Thereof" The present application incorporates herein by reference the disclosures of each of the above-referenced applications in their entireties.

FIELD OF THE DISCLOSURE

Embodiments of the present disclosure are directed generally to monofilament medical implants, and systems and methods for their delivery. Some embodiments of said systems may be automatic. Some embodiments are directed to embolic protection devices, and systems and methods for the delivery thereof. Some of the embodiments are directed at preventing embolic stroke.

BACKGROUND OF THE DISCLOSURE

Expandable implantable devices are often used for opening and closing passageways or orifices within the vascular, urinary, or gastrointestinal (GI) systems. Examples include vascular and GI stents for opening occlusions, left atrial appendage (LAA) and patent foramen ovale (PFO) occluding devices, and others. Such implantable devices typically consist of a scaffold that is introduced in a collapsed state and is expanded to a desired configuration at a target organ.

U.S. Provisional Patent Application 61/746,423, filed Dec. 27, 2012, to Yodfat and Shinar, assigned to Javelin Medical Ltd., discloses expandable devices and a method for implanting the devices within the body. Some of the embodiments of that disclosure are directed to devices made of super-elastic metal (e.g., nitinol) configured into a monofilament which is spatially bent and/or twisted (e.g., upon delivery). Such devices have two operating states—a contracted state (undeployed) and an expanded state (deployed). The devices may be implanted using a delivery system comprising (for example) a rigid needle having a preferred diameter of <1 mm (3 French, 0.04") and a sharp distal end. The devices may be preassembled within the needle in their stretched, substantially-linear, undeployed state and positioned at the needle's distal end. A pusher, in the form of an elongated rod, may also be preassembled within the needle, extending from proximally to the proximal end of the needle to the proximal end of the device. The implantation of the device may be performed by piercing the skin and underlying tissues and advancing the needle to the target organ under ultrasound guidance. At the desired location, the device may be exteriorized by retracting the needle with respect to the patient, pushing the pusher with respect to the patient, or both. This creates relative motion between the needle and the pusher, thereby exteriorizing the device. During the exteriorization process the device assumes its expanded deployed state within the target.

In a preferred embodiment, the device may be used as a filtering device (hereinafter "filtering device" or "embolic protection device") for cardio-embolic stroke prevention. Such devices may be implanted at both carotid arteries to protect the brain from emboli originating in the heart, aorta, or other proximal large vessels.

The deployed state of the stroke prevention filtering device, according to those disclosed embodiments, may have the shape of a helical spring roughly occupying a spherical shell, with straight short ends extending from each side of the helix at the in the direction of the helix's principal axis of symmetry. Anchors for securing the filtering device to the carotid walls may reside at both ends. The anchors may also be made radiopaque or echogenic to provide visibility. When deployed, the device resides in transverse orientation within carotid artery lumen, the two device ends pierce the artery walls, and both anchors reside externally to lumen.

In the undeployed state, the device according to some embodiments, including anchors, resides within the lumen of the needle. The distal anchor is connected to the distal end of the helical spring and resides at distal end of the needle. The proximal anchor may be connected to the proximal end of the helical spring and reside closer to the proximal end of the needle than to the distal end of the device. After deployment, the anchors may self-expand to their deployed state.

Implantation, according to some embodiments, comprises insertion of the needle with the preassembled filtering device through the skin of the neck and transversally bisecting the carotid artery. Subsequently, the needle is retracted and the filtering device is exteriorized by the pusher. The filtering device assumes its deployed shape and is anchored externally to the carotid wall at both ends.

Experience shows that when the device is exteriorized from the needle, its distal end, at times, may rotate, bend, or twist. Therefore, whenever the device is exteriorized after its distal end is anchored in the carotid wall, this tendency to rotate, bend, or twist creates torque on the anchor. Accordingly, such torque might damage the tissue surrounding the anchor. Alternatively, the anchor may remain motionless but torsion may accumulate in the monofilament component of the device, thereby preventing it from assuming the desired deployed helical shape: The windings of the helix may distort and cross over.

Thus, there is a need for a helical filtering device that can be inserted into the carotid arteries in a safe and reproducible manner.

There is also a need to provide a helical filtering device that can transition from a helical shape to a substantially linear shape and back, without plastically deforming.

There is also a need for a helical filtering device (or any other monofilament device) in which torsion does not accumulate during deployment.

There is also a need for a helical filtering device (or any other monofilament device) comprising at least one bearing.

There is also a need for a system and method for safe implantation of a monofilament helical filtering device (or any other monofilament device) such that damage to the vessel walls and surrounding tissues is avoided.

There is also a need to provide a system for automatically implanting a filtering device (or any other monofilament device) in a safe and reproducible manner.

There is also a need to provide a system for automatically implanting a filtering device (or any other monofilament device) using a single hand.

There is also a need to provide a system for implanting a filtering device (or any other monofilament device), the system including housing and a user interface.

There is also a need for a system for implanting a filtering device (or any other monofilament device), the system including one or more sensors. Sensors may provide an indication of the needle position within the body or an indication of the deployment status or progression.

There is also a need for a system for implanting a filtering device (or any other monofilament device) that prevents the build-up of torsion in the filtering device by synchronizing device exteriorization and device rotation, bending, or twisting.

There is also a need for a system for implanting a filtering device (or any other monofilament device) that prevents the build-up of torsion in the filtering device by synchronizing device exteriorization and device rotation, bending, or twisting, wherein the system comprises a power supply, a motor, a controller, a driving mechanism, a sensor, and a user interface.

SUMMARY OF THE DISCLOSURE

In some embodiments, the filtering device is a monofilament made of a super-elastic alloy (i.e. nitinol), and has a circular cross section. In the deployed state the device is shaped as a helix (coil, spring, or their like) tracing a spherical shell, with two straight short monofilament segments extending from each helix end. The segments are oriented substantially collinear with the helix's principal axis of symmetry.

In some embodiments, each end-segment may comprise an end piece. Each end piece may comprise one or more of a radiopaque marker, an echogenic marker, an anchor, and/or a bearing. The bearing may have an axle, which may be integral with the monofilament, and housing. The axle may freely rotate within the housing, thereby eliminating the build-up of deleterious torsion during device deployment.

some embodiments, in the undeployed state, the helix-shaped monofilament is stretched to a substantially linear shape and assembled within the lumen of a needle. The distal end piece resides at the distal sharp end of the needle and proximal end piece resides closer to the proximal end of needle than the distal end of the device. A straight rod ("pusher") is assembled within proximal side of needle; the pusher distal end is in contact with the proximal end of the filtering device.

In some embodiments, implantation comprises insertion of the needle, with the filtering device preassembled, through the neck skin, and transversally bisecting the carotid artery. Subsequently, retraction of needle and/or pusher advancement exteriorize the filtering device from needle may be according to the following sequence:

1—The distal end piece is deployed externally to carotid lumen and anchored within surrounding tissue. The end piece may comprise a bearing enabling free rotation of the bearing axle around longitudinal axis, thereby avoiding the build-up of torsion in the monofilament.

2—The helical monofilament is deployed within the carotid lumen. During deployment the helix rotates roughly around its axis of symmetry, with distal end of the helix (axle) serving as a pivot point.

3—The proximal end piece is deployed externally to proximal side (close to skin) of the carotid lumen.

In some embodiments, torsion release may be achieved by concomitant needle retraction, needle rotation, and pusher advancement during filtering device exteriorization.

In some embodiments, implantation of the filtering device (or any other monofilament device) may be performed using a system that automatically synchronizes needle retraction, filtering device exteriorization, filtering device rotation, bending, or twisting (and corresponding torsion build-up prevention or release) during filtering device implantation. The system may comprise housing, a power supply, a motor, a control unit, and a driving mechanism. In some embodiments, the system comprises a reusable element. The needle and filtering device (disposables) may be pre-assembled before insertion and the needle is disposed after use. The driving mechanism may comprise gears that are engaged with proximal ends of the needle and the pusher. Upon operator activation, the controller operates a motor, synchronizes the needle and/or pusher rotation, and needle retraction. The system may include user interface components (operating buttons, screen, etc.), sensors (i.e. pressure sensor for safe positioning of needle end within artery), and indication means for providing better operator control during insertion.

Advantages of Some of the Embodiments

Embodiments according to the present disclosure have several important advantages over prior art:

Various embodiments of filtering devices according to the present disclosure may be safely inserted by providing a mechanism to prevent the build-up of torsion or to release accumulated torsion within the device.

Various embodiments of monofilament device implantation systems according to the present disclosure may provide safe and reproducible device implantation by automatically executing any combination of the following motions: needle retraction, needle advancement, device retraction, device advancement, device rotation, device bending, or device twisting. In particular, the build-up of torsion in the device may be prevented, and accumulated torsion may be released.

BRIEF DESCRIPTION OF THE DRAWINGS

The invention may be better understood with reference to the accompanying drawings and subsequently provided detailed description:

FIG. 3A depicts a schematic rendering of the undeployed state of an end piece according to some embodiments of the present disclosure.

FIG. 3B depicts a schematic rendering of the deployed state of an end piece according to some embodiments of the present disclosure.

FIGS. 6A-6E depict an apparatus and method according to some embodiments of the present disclosure, which are intended for implanting a monofilament filtering device according to some embodiments of the present disclosure.

FIGS. 10A and 10B depict a monofilament filtering device according to some embodiments of the present disclosure in operation.

DETAILED DESCRIPTION OF SOME OF THE EMBODIMENTS

Figure 1B:
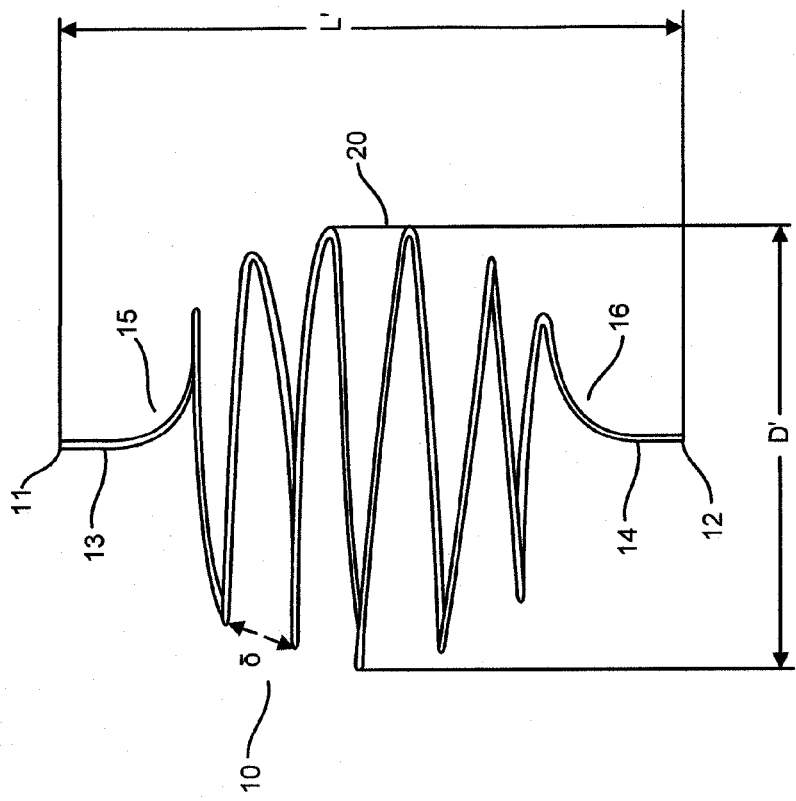
FIG. 1B depicts the deployed (helical) state of the monofilament filtering device of FIG. 1A.
Figure 1A:
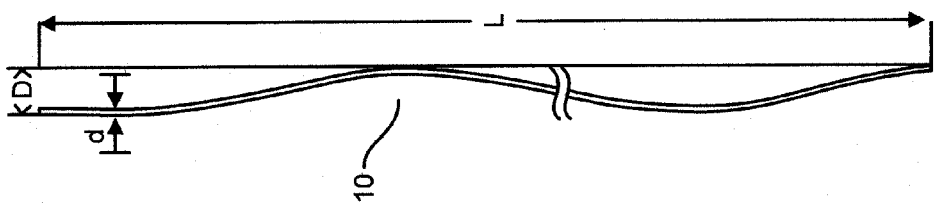
FIG. 1A depicts the undeployed state of a monofilament filtering device according to some embodiments of the present disclosure.

Reference is now made to FIG. 1A, which depicts some embodiments of the undeployed state of a filtering device (embolic protection device) of the present disclosure. Filtering device 10, configured to be implanted in a body vessel, can be a filament of cylindrical shape. However, cross sectional shapes other than circular are also possible.

In some embodiments, the length of the filament from which filtering device 10 is made may be greater than the diameter of the body vessel for which it is intended. Thus, if implanting the filtering device in a vein or an artery having a diameter of 7 mm, then the length of the filament may be, for example, in the range of about 7 to about 300 mm.

In some embodiments, the diameter of the filament from which filtering device 10 is made may be substantially less than its length. For implantation into a blood vessel, the filament diameter may be chosen of a size sufficient so as to not to cause blood coagulation. Therefore, the filament diameter, according to some embodiments, is less than about 0.5 mm, and more specifically less than about 0.2 mm, and even more specifically, less than about 0.15 mm.

In some embodiments, the undeployed state of device 10 may assume any shape that fits within the lumen of a tube having a length L and an inner diameter D such that L is much greater than D. (the terms "substantially linear" or "substantially straight" as used herein refer to all such shapes.) For example, length L can be in the range of about 10 to about 300 mm, whereas the diameter D can be in the range of about 0.05 to about 0.7 mm.

In some embodiments, the undeployed state of device 10 may assume, for example, the shape of a substantially straight line. It may also assume a shape resembling a helix in which the pitch (that is, the vertical distance between consecutive windings) may be much larger than the helix diameter (that is, the diameter of the smallest cylinder in which the helix might fit).

Reference is now made to FIG. 1B, which depicts an embodiment of the deployed state of a filtering device of the present disclosure. In the deployed state, filtering device 10 may assume the shape of a coil or a spring (helix). This coil shape may have windings or turns that vary in diameter. The windings may approximately trace the shape of a spherical shell.

The deployed length L' of filtering device 10 may be greater than the diameter of the body vessel for which it is intended. Thus, if implanting the filtering device in a vein or an artery having a diameter of about 7 mm, then the deployed length L' can be, for example, in the range of about 7 to about 20 mm. The deployed diameter D' of filtering device 10 may be less than or approximately equal to the diameter of the target vessel at the implantation site. For example, if implanting the filtering device in a vein or an artery having a diameter of about 7 mm then the diameter D' may be in the range of about 5 mm to about 8 mm.

In the deployed state, the "north-south" axis connecting distal end 11 and proximal end 12 of device 10 is substantially perpendicular to the plane approximately defined by some of the spring windings. The distal segment 13 and the proximal segment 14 of device 10 may be substantially collinear with the north-south axis.

The distal turn 15 of device 10 may reside in a plane containing the north-south axis. Likewise, the proximal turn 16 in device 10 may also reside in a plane containing the north-south axis. The two planes may, but do not have to, be one and the same. All of the remaining turns in device 10 may reside in planes that are approximately, but not necessarily exactly, perpendicular to the north-south axis.

Device 10 may be configured such that in the deployed state the radius of curvature at any point along its length is greater than or equal to a critical value $R_c$. This critical value may be assigned such that the strain suffered at any point of device 10 is less than or equal to the critical strain required to bring about an elastic-to-plastic transformation. In this way device 10 may be able to suffer a transition from the deployed shape to the undeployed shape and back without substantial difference between the initial and final deployed shapes. For example, if the filament from which device 10 is made has a circular cross section having diameter d, and the material from which device 10 is made has critical strain $\varepsilon$, then the critical value $R_c$ may be given by $R_c = d/2\varepsilon$. Therefore, if, for example, device 10 is made from superelastic nitinol having critical strain £ of about 0.08, and the filament diameter d is about 0.15 mm, then the critical radius of curvature will be roughly about 0.94 mm.

The deployed state of device 10 may be configured to trap embolic material having typical size that is larger than the distance δ between consecutive windings. Whenever device 10 is configured to protect a patient from major embolic stroke, device 10 is made to trap emboli exceeding about 1-2 mm in size. In this case the distance δ is less than about 1.5 mm, and, more specifically, in the range of about 0.7 mm and about 1.5 mm.

Filtering device 10 may be configured to be relatively stiff or, in some embodiments, relatively flexible. Alternatively, filtering device 10 may be configured to assume any degree of flexibility. In the deployed shape, filtering device 10 may possess either a low spring constant or a high spring constant. Alternatively, in the deployed state, filtering device 10 may be configured to any value for its corresponding spring constant.

Filtering device 10, according to some embodiments, can be configured as a solid filament. Alternatively, it can be configured as a tube having a hollow lumen, or as a tube having its ends closed-off, thereby leaving an elongated air-space inside filtering device 10. Leaving an air-space inside filtering device 10 may have the advantage of making filtering device 10 more echogenic and therefore more highly visible by ultrasound imaging. Filtering device 10 may possess an echogenic marker or a radiopaque marker.

Filtering device 10 can be made out of any suitable biocompatible material, such as metal, plastic, or natural polymer. Suitable metals include shape-memory alloys and super-elastic alloys (nitinol). Suitable polymers may include shape memory polymers or super-elastic polymers.

A filtering device according to some embodiments of the present disclosure is substantially similar to filtering device 10, except for one or more of the following differences: part or all of distal segment 13 may be lacking, part or all of distal turn 15 may be lacking, part or all of proximal segment 14 may be lacking, and part or all of proximal turn 16 may be lacking. For example, a filtering device substantially similar to 10 but lacking distal segment 13 and distal turn 15 may be particularly suitable for implantation through a single puncture in a target vessel. In such an embodiment, all device parts except perhaps for proximal segment 14 may lie entirely inside the vessel lumen or walls. Distal end 11 may comprise a non-traumatic tip, or a short, sharp end configured to anchor in the vessel wall without breaching it completely.

Figure 2B:
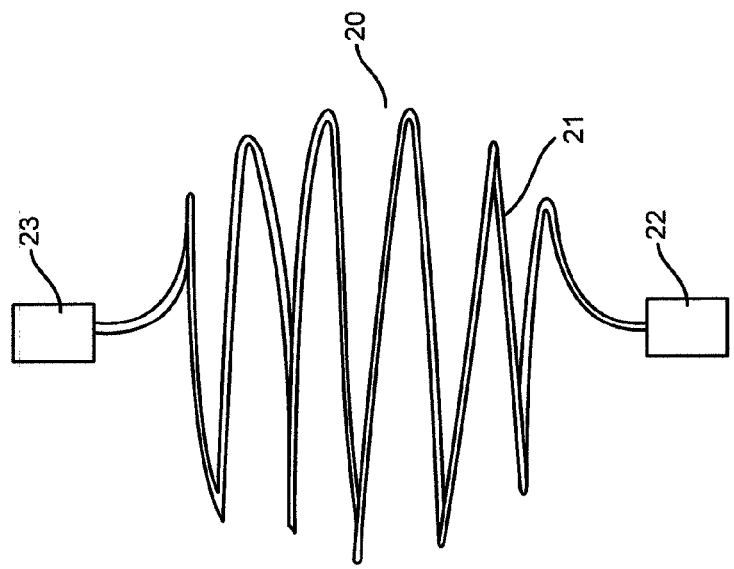
FIG. 2B depicts the undeployed state of a monofilament filtering device comprising end pieces according to some embodiments of the present disclosure.
Figure 2A:
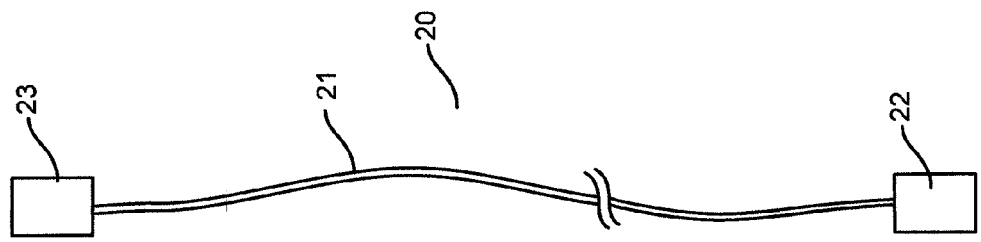
FIG. 2A depicts the undeployed state of a monofilament filtering device comprising end pieces according to some embodiments of the present disclosure.

Reference is now made to FIGS. 2A and 2B, which respectively represent the undeployed and the deployed states of another embodiment of the filtering device of the present disclosure. Filtering device 20 is substantially similar to filtering device 10 of FIGS. 1A and 1B: device 20 comprises a filament 21 that is substantially similar to the filament from which device 10 is made. However, device 20 may also comprise one or more of a first end piece 22 residing at one end of filament 21, and a second end piece 23 residing at the opposite end of filament 21.

In the undeployed state (FIG. 2A), filtering device 20, including end-pieces 22 and 23, may be configured to reside in the lumen of a hollow needle. Upon exteriorization from such a needle (FIG. 2B), filtering device 22 may assume a deployed shape substantially similar to that of filtering device 10, and end-pieces 22 and 23 may assume a shape (but not required to) that is different from their shape in the undeployed state of device 20.

Reference is now made to FIG. 3A, which depicts a schematic representation of end piece 23 in the undeployed state according to some embodiments. End piece 23 may comprise one or more of the following: an anchor 31, a radiopaque marker 32, an echogenic marker 33, and a bearing 34. End piece 23 may also comprise a non-traumatic tip, such as a ball-shaped protrusion made of metal.

Anchor 31 may comprise any means known in the art for attaching a foreign body to living tissue. For example anchor 31 may comprise a roughened surface, one or more barbs, one or more micro-barbs, one or more hook, a hydrogel bulge configured to enlarge upon contact with an aqueous environment, or their likes. Anchor 31 may be configured to change its shape upon transition from the undeployed state to the deployed state of device 20 (FIG. 3B). Anchor 31 may comprise a biocompatible metal, a biocompatible polymer, a shape memory material, a super elastic material (e.g. super elastic nitinol) or any combination thereof.

Radiopaque marker 32 may comprise a biocompatible radiopaque material, such as gold or platinum.

Echogenic marker 33 may comprise a biocompatible echogenic material, such as tantalum. The marker 33 may comprise an echogenic coating comprising air microbubbles, cornerstone reflectors, or any other means known in the art to increase echogenicity. Upon transition from the undeployed state to the deployed state of device 20, marker 33 may retain its shape. Alternatively, the shape of marker 33 may change upon transition from the undeployed to the deployed state.

Bearing 34 may comprise an axle 35 and a housing 36. Axle 35 may be configured to freely rotate within housing 35. Alternatively, axle 35 may be configured to rotate within housing 35 with any pre-specified degree of friction. Axle 35 may be rigidly connected to an end of filament 21. Alternatively, axle 35 may be integral with an end of filament 21. Housing 36 may be rigidly connected to anchor 31. In this way, upon application of torque to axle 35, the axle may rotate inside housing 36, and housing 36 may remain substantially motionless with respect to the tissue in which it resides.

Bearing 34 may comprise any mechanism known in the art for constraining relative motion between the axle and the housing to only a desired motion. For example, bearing 34 may comprise a plain bearing, a bushing, a journal bearing, a sleeve bearing, a rifle bearing, a rolling-element bearing, a jewel bearing, and a flexure bearing.

End piece 22 may be the same as or different from end piece 23. Similarly to end piece 23, end piece 22 may comprise one or more of an anchor, a radiopaque marker, an echogenic marker, and a bearing.

Figure 4B:
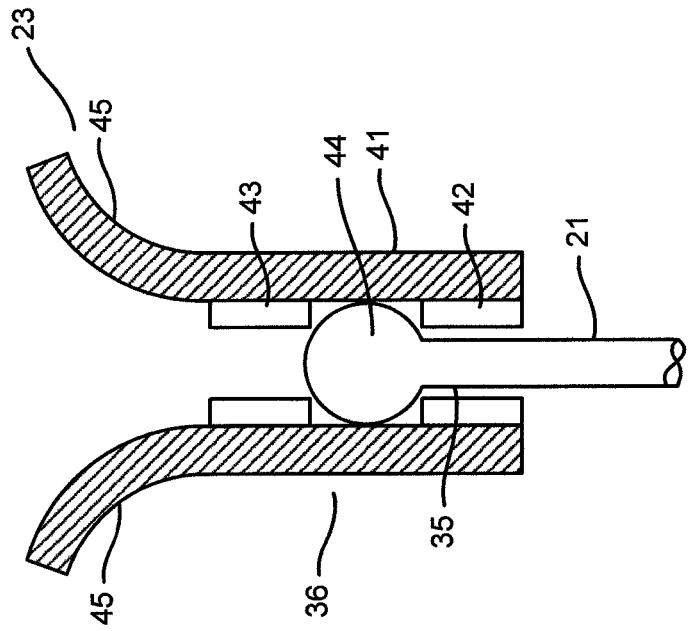
FIG. 4B depicts the deployed state of an end piece according to some embodiments of the present disclosure.

We note that different components in each end piece need not be physically distinct: for example, the housing of the bearing can also serve as an anchor, the radiopaque marker and the echogenic marker may be one and the same, the bearing may serve to provide radiopacity or echogenicity, and so forth. To illustrate this point, reference is now made FIGS. 4A and 4B, which represent an embodiment of end piece 23 according to the present disclosure, and to FIGS. 5A and 5B, which represent an embodiment of end piece 22 according to the present disclosure.

Figure 4A:
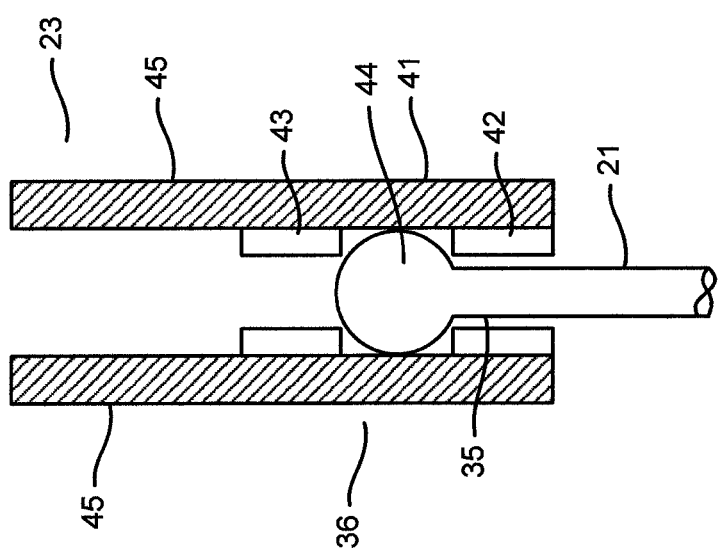
FIG. 4A depicts the undeployed state of an end piece according to some embodiments of the present disclosure.
Figure 5B:
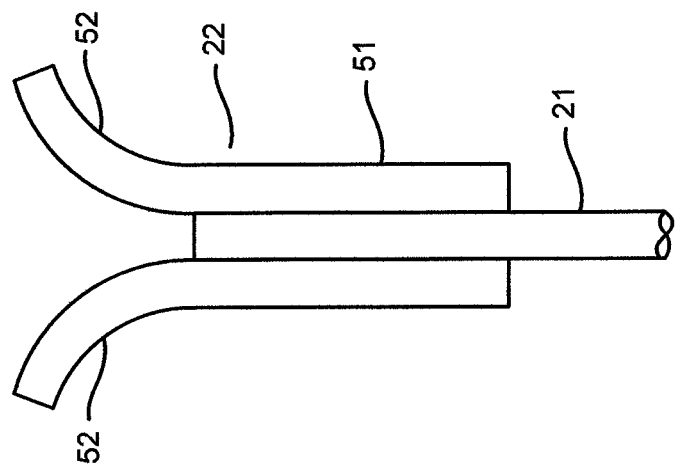
FIG. 5B depicts the deployed state of another end piece according to some embodiments of the present disclosure.

FIG. 4A depicts the undeployed state of a particular embodiment of end piece 23, according to the present disclosure. End piece 23 may comprise an external cylinder 41, prongs 45, a proximal ring 42, a distal ring 43, a ball 44, and axle 35. External cylinder 41 and prongs 45 may be integral with each other. They may be made from a shape memory or super-elastic alloy, such as nitinol. Upon transition of device 20 from the undeployed to the deployed state, prongs 45 extend outwards, thereby anchoring end piece 23 in the tissue in which it is implanted. The proximal part of cylinder 41, proximal ring 42, and distal ring 43 may be rigidly connected to each other to form a bearing housing 36. Rings 42 and 43 can each be made from a radiopaque and or echogenic material, such as god, platinum, or tantalum. The end of filament 21 may be rigidly connected to, and may be integral with, ball 44, which can be made out of metal, a polymer, an alloy, a shape memory material, or a super elastic material. Together, filament end 21 and ball 44 provide a bearing axle 35. The axle 35 is free to rotate within housing 36 more or less around the housing's principal axis of symmetry. However, in some embodiments, rings 42 and 43 substantially prevent all other relative motions of axle 35 with respect to housing 36. Housing 36 and axle 35 together provide a bearing.

Figure 5A:
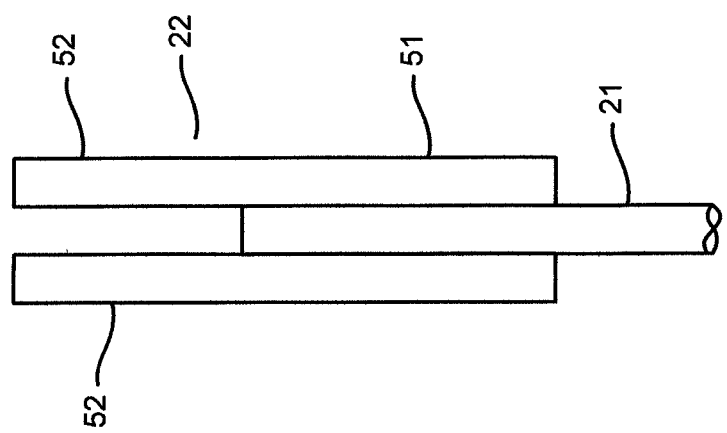
FIG. 5A depicts the undeployed state of another end piece according to some embodiments of the present disclosure.

FIG. 5A depicts the undeployed state of some embodiments of end piece 22, according to the present disclosure. End piece 22 may comprise an external cylinder 51, and prongs 52, which may be integral with the cylinder. Both the prongs and the cylinder can be made from a shape memory or super-elastic material, such as nitinol. External cylinder 51 may be rigidly connected to the end of filament 21 using any known connection means known in the art, such as crimping, welding, soldering, gluing, and their likes. The external surface of cylinder 51 may be coated with an echogenic coating, or carry cornerstone reflectors. In this way, end piece 22 may comprise an anchor and an echogenic marker. However, the embodiment of end piece 22 presented in FIGS. 5A and 5B does not comprise a bearing.

Reference is now made to FIGS. 6A-6E, which illustrate a system and a method according to some embodiments of the present disclosure for providing embolic protection according to some embodiments of the present disclosure. The system and method are particularly suitable for delivering a filtering device 20 comprising at least one end piece incorporating a bearing. The at least one end piece incorporating a bearing enables torsion in filament 21 of device 20 to be controllably released during device implantation, thereby providing for a controlled and robust implantation procedure.

FIG. 6A depicts a system 60 configured to implant a filtering device 20 in a body vessel 61. System 60 comprises a hollow needle 62, a pusher 63, and filtering device 20. Taken together, the hollow needle and the pusher are a delivery device. Hollow needle 62 has a sharp end 63 configured to pierce skin 64, subcutaneous tissue 65, and body vessel 61 of a patient. Needle 62 may have a needle handle 66 located at its proximal end 67. The needle handle 66 may be rigidly connected to needle 62. Pusher 63 may have a pusher handle 68 located at its proximal end.

Hollow needle 62 may have a very small inner and outer diameter. For example, if the maximal collapsed diameter of undeployed filtering device 20 is about 200 to about 400 microns, the inner diameter of hollow needle 62 may be in the range of about 200 to about 900 microns, and the outer diameter of hollow needle 62 can be in the range of about 300 to about 1000 microns. More specifically, the inner diameter of hollow needle 62 may be in the range of about 200 to about 400 microns, and the outer diameter of needle 62 may be in the range of about 300 to about 600 microns. Thus, the puncture holes made by hollow needle 41 in a patient's tissue may be sufficiently small (about 400 to about 800 microns) as to be self-sealing.

Hollow needle 62 may be made out of any suitable biocompatible material, such as, for example, steel. Pusher 63 may also be made out of a metal such as steel. Handles 66 and 68 may be made out of plastic.

In the absence of external load, filtering device 20, in some embodiments, assumes the deployed shape of FIG. 2B. To transform device 20 to the undeployed state, it may be stretched by applying axial force at both its ends using a special jig (not shown). The stretched device may then be inserted into the lumen of needle 62 by sliding the needle over the stretched, undeployed device. Twisting device 20 before or during insertion into needle 62 is also possible.

Figure 6E:
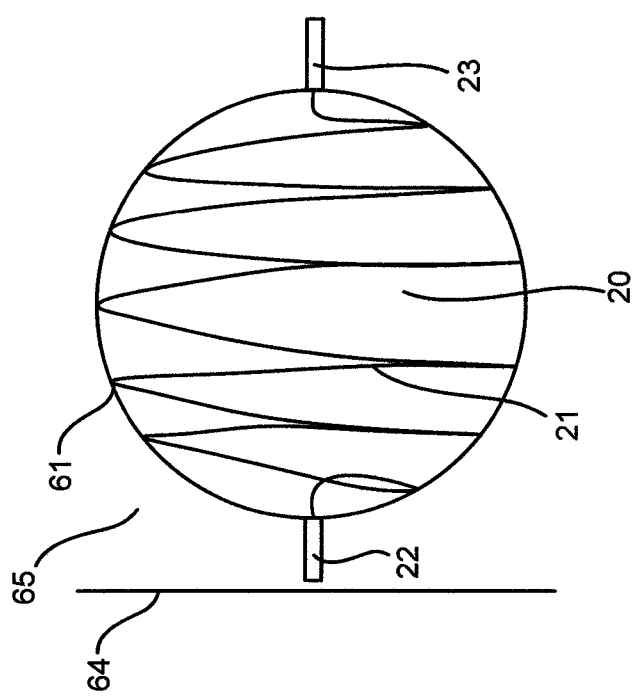

Both filtering device 20 and pusher 63 may be slidable within the lumen of hollow needle 62. Prior to deployment, filtering device 20 is located inside the lumen of needle 62 near its distal end 63. The distal end 68 of pusher 63 is also located inside the lumen of hollow needle 62. The distal end 68 of pusher 63 is in contact with the proximal end of end piece 22 of device 20. After deployment, as depicted in FIG. 6E, filtering device 20 may be exteriorized from hollow needle 62, and the distal end of pusher 63 roughly coincides with distal end 63 of hollow needle 62.

The implantation of filtering device 20 in body vessel 61 may proceed as follows. First, a physician determines that it is desirable to implant filtering device 20 in body vessel 61. Under the guidance of a suitable imaging modality (not shown), such as, for example, ultrasound, high resolution ultrasound, or CT scanning, or without imaging guidance at all, the operator punctures skin 64 adjacent to vessel 61 using the sharp end 63 of needle 62. Note that delivery device 60 is in the configuration depicted in FIG. 6A, that is, with filtering device 20 housed near the distal end of hollow needle 62, in its undeployed state. The operator then carefully advances delivery device 60 through the subcutaneous tissue, and transversely punctures vessel 61 at approximately diametrically-opposed sites 690 and 691. The first puncture 690 of vessel 61 is made on its side closer to skin 64, and the second puncture 691 is made on the diametrically-opposite side. The sharp end of needle 63 may then be advanced a few more millimeters interiorly into the patient, so that end piece 23 may be exterior to the lumen of vessel 61. This situation is depicted in FIG. 6A.

Next, the operator holds pusher 63 substantially motionless while retracting hollow needle 62 backwards, away from the patient. This can be done with the aid of handles 66 and 68. In this way, end piece 23 of device 20 is exteriorized from needle 62. It then assumes its deployed state in the tissue proximate second puncture 691, thereby potentially anchoring the distal end of device 20 in the tissue. The needle may then be retracted until its distal end 63 roughly coincides with proximal puncture 690. This situation is depicted in FIG. 6B.

To exteriorize the remainder of device 20 from hollow needle 62, the operator advances pusher 63 towards the distal end 63 of needle 62 while holding the needle still. As device 20 is exteriorized from the needle, it gradually assumes its deployed, spring-like shape-like shape. This situation is depicted in FIG. 6C.

In some embodiments, exteriorizing device 20 may create torque along the principal axis of end-piece 23. In such embodiments, it may be advantageous for end piece 23 to comprise a bearing 34, thereby enabling the strain (torsion) pre-existing in filament 21 to release. This may also prevent torsion from building up during the exteriorization process. In such embodiments, the distal end of filament 21 rotates with end piece 23 as a pivot point while device 20 is exteriorized. The operator stops pushing the pusher once filament 21 is essentially exteriorized from needle 62 into the lumen of vessel 61, and end piece 22 is situated, still inside the lumen of needle 62, proximate its implantation site. The situation is then as depicted in FIG. 6D.

In some embodiments, to complete the implantation procedure, the operator holds pusher 63 steady while retracting needle 62 over the pusher. This causes the end piece 22 to be exteriorized at its implantation site and assume its deployed shape. Once the entire device 20 is exteriorized and implanted in its deployed state, both needle 62 and pusher 63 are exteriorized from the patient's body. This completes the implantation procedure for some embodiments, as depicted in FIG. 6E. Note that for some embodiments, because both the filtering device 20 and hollow needle 62 are of a diameter which is sufficiently small, all of the holes and the punctures made in body tissues during the procedure may be self-sealing. Therefore, the suturing or sealing of holes and punctures thus made is unnecessary. If it is determined that one or more additional filtering devices should be implanted in one or more additional implantation sites the procedure may be performed again, essentially as described above.

The system and implantation method corresponding to embodiment 10 of the filtering device are substantially similar to those described for delivery device 20 and its associated method of use, as described above. Therefore, a detailed description of delivery devices and implantation procedures corresponding to filtering device 10 is omitted.

In some embodiments, the implantation of filtering device 20 by means of system 60 in a body vessel may involve making a single puncture in the vessel wall, as opposed to two roughly diametrically opposed punctures: The operator makes a single proximal puncture in the vessel wall using needle 62, or using distal end-piece 23, the distal end of which may be sharp. The operator then places the distal tip of needle 62, or the distal tip of end-piece 23, in the lumen of the vessel. Subsequently, the operator advances device 20 into the vessel lumen by pushing pusher 63 while holding needle 62 steady, until only the proximal end-piece 22 remains inside needle 62. Finally, exteriorization of device 20 from needle 62 is completed by, for example, retracting needle 62 while maintaining pusher 63 in place. Upon the completion of the exteriorization of device 20 from needle 62, end piece 23 may be located anywhere inside the lumen of the vessel. For example, end piece 23 may appose the vessel wall. For example, end piece 23 may appose the vessel wall at a location roughly diametrically opposed to the puncture site. For example, end-piece 23 may partially or completely penetrate the vessel wall. For example, end-piece 23 may completely penetrate the vessel wall. Proximal end piece 22 may be located outside the lumen of the vessel, across the lumen of the vessel, or inside the lumen of the vessel. Typically, end piece 22 may comprise an anchor configured to prevent the migration of device 22 by securing it to the tissue of the vessel wall, or to tissue proximate the vessel wall. Upon completion of the exteriorization step, needle 62 and pusher 63 are withdrawn from the patient's body, and the implantation of device 20 is complete.

Figure 7:
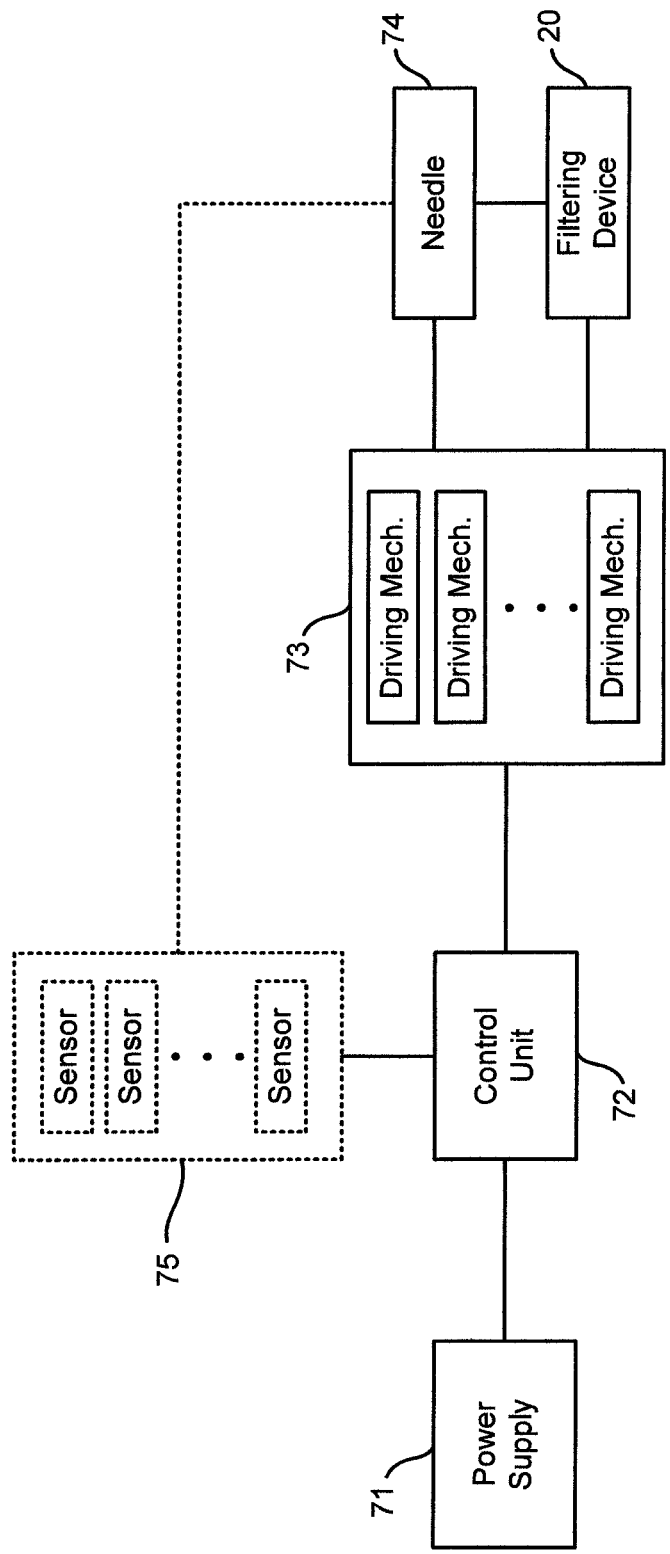
FIG. 7 is a block diagram of an automatic system according to some embodiments of the present disclosure, which is intended for implanting a monofilament filtering device (or any other monofilament device) according to some embodiments of the present disclosure.

Reference is now made to FIG. 7, which provides a schematic block diagram of some embodiments according to the present disclosure of an automatic system for providing embolic protection according to some embodiments of the present disclosure. In some embodiments, mandatory blocks or components have solid outlines in FIG. 7, whereas optional blocks or components have dashed outlines. Solid lines connecting blocks represent information flow, power flow, or mechanical force transmission between blocks. Dashed lines connecting blocks represent optional information flow, power flow, or mechanical force transmission between blocks. Automatic system 70 may provide for a controlled and robust implantation of filtering device 20 (or filtering device 10), and for reduced inter-operator variability.

Accordingly, system 70 comprises a power supply 71, a control unit 72, one or more driving mechanism 73, hollow needle 74, and filtering device 20. Optionally, system 70 may also comprise one or more sensors 75. Taken together, power supply 71, control unit 72, one or more driving mechanism 73, and hollow needle 74 comprise a delivery device.

The power supply 71, control unit 72, and one or more driving mechanism 73, may reside in an external unit, which is external to the patient's body. Needle 74, filtering device 20, and optionally, one or more sensor 75 may be completely or partially located inside the patient's body during the device implantation procedure. The patient-external components may be housed in an ergonomic handle (not shown) and may or may not be sterile. The patient internal components may be sterile. System 70 may be completely disposable. System 70 may also comprise both reusable and disposable components. For example, the externally-residing components may be reusable, whereas the internally residing components may be disposable.

Power supply 71 may be an electrical or mechanical source of (free) energy. Power supply 71 may be a direct current source, such as a battery. Power supply 71 may also be an alternating current source.

Control unit 72 may comprise an input/output device, a central processing unit, a digital memory (all not shown), and any type of an analog or digital electronic controller (not shown), such as a computer processor programmed to cause any conceivable motion to filtering device 20. For example, control unit 72, by means of one or more driving mechanism 73, may cause filtering device 20 to bend, twist, rotate, translate, or any combination of such motions. The controller may be an open loop controller, a closed loop controller, a proportional controller, a proportional integral derivative controller, or any other type of controller known in the art. Control unit 72 may store and implement any predetermined program of filtering device motions. Control unit 72 may optionally also receive inputs from one or more sensors 75, and implement this information in governing the motion of filtering device 20.

One or more driving mechanism 73 may comprise one or more motor and one or more transmission. The one or more transmission may couple the one or more motor to hollow needle 74 and/or filtering device 20. The one or more driving mechanism 73 may be configured to rotate needle 74 (thereby causing some or all of filtering device 20 to rotate). Alternatively, one or more driving mechanism 73 may cause filtering device 20 to rotate by direct mechanical coupling between the driving mechanism and the filtering device. One or more driving mechanism 73 may be configured to cause needle 74 to advance or retract. One or more driving mechanism 73 may be configured to cause filtering device 20 to advance or retract within needle 74, or to move together with the needle such that there is no relative motion between the filtering device and the needle. One or more driving mechanism 73 may be configured to cause filtering device 20 to be exteriorized from needle 74. Mechanical coupling between one or more driving mechanism 73 and filtering device 20 may be made by means of a pusher, a rotating shaft, a spring, and their likes.

One or more driving mechanism 73 may comprise one or more motor. The motor or motors may be of the following types: a DC motor, a universal motor, an AC motor, a stepper motor, a permanent magnet motor, a brushed DC motor, a brushless DC motor, a switched reluctance motor, a coreless DC motor, a printed armature or pancake DC motor, an AC motor with sliding rotor, a synchronous electric motor, an induction motor, a doubly fed electric motor, a singly fed electric motor, and a torque motor. Signals, which may be generated by control unit 72 according to a predetermined program, or by a program optionally configured to receive signals from optional one or more sensor 75, may be transmitted to one or more driving mechanism 73. One or more driving mechanism 73 may then cause filtering device 20 to move in accordance with the predetermined program or sensor-signal-sensitive program, thereby achieving automatic device implantation.

Hollow needle 74 may be substantially similar to hollow needle 62 of FIGS. 6A-6E. Therefore, we shall omit its detailed description here. Filtering device 20 may reside in its undeployed state inside the lumen of needle 74.

One or more optional sensors 75 may comprise one or more of: a chemical sensor, a physical sensor, a mechanical sensor, a physiological sensor, an electrophysiological sensor, and a pressure sensor. Optional one or more sensors 75 may be mounted on needle 74. Optional one or more sensors 75 may provide information on whether the tip of needle 74 is within the lumen of a vessel, such as, for example, a blood vessel, or within the surrounding tissue. A pressure sensor may serve this function because the blood pressure (that is, the pressure inside the lumen of a blood vessel) is different from the pressure in the surrounding tissue. This information may provide extra safety: for example, control system 72 may be preprogrammed to prevent the exteriorization of an end unit of filtering device 20 unless the pressure sensed is within ranges typical for blood pressure in the target vessel.

Optional one or more sensors 75 may sense the stage of the heart cycle. As it might be advantageous to exteriorize the filtering device 20 only when the target vessel is in a relaxed state (corresponding to a heart diastole), optional one or more sensor 75 may comprise an electro-cardiogram (ECG) sensor.

In some embodiments, the implantation of filtering device 20 by means of automatic system 70 in a body vessel may proceed as follows. First, a physician determines that it is desirable to implant filtering device 20 in the body vessel. Under the guidance of a suitable imaging modality (not shown), such as, for example, ultrasound, high resolution ultrasound, or CT scanning, or without imaging guidance at all, the operator punctures the skin adjacent to the vessel 61 using the sharp end of needle 74. The operator then carefully advances delivery device 70 through the subcutaneous tissue, and transversely punctures the vessel at approximately diametrically-opposed sites. The sharp end of needle 74 may then be advanced a few more millimeters interiorly into the patient, so that end piece 23 is exterior to the lumen of the vessel. Once this positioning is achieved, the operator instructs control unit 72 to execute a predetermined program (which optionally depends on inputs from one or more sensor 75), which causes device 20 to be properly exteriorized, such that the end pieces are external to the vessel lumen and the filament of device 20 is properly arranged within the lumen. Once the device 20 is properly exteriorized, the operator extracts system 70 from the patient's body.

In some embodiments, the implantation of filtering device 20 by means of automatic system 70 in a body vessel may proceed as in the previous paragraph until the step in which the operator punctures the body vessel. Instead of making two substantially diametrically-opposed punctures in the vessel wall, the operator makes a single puncture in the vessel wall using needle 74, or using distal end-piece 23. The operator then places the distal tip of needle 74, or the distal tip of end-piece 23, in the lumen of the vessel. Subsequently, the operator instructs control unit 72 to execute a predetermined program (which optionally depends on inputs from one or more sensor 75), which causes device 20 to be properly exteriorized. Upon the completion of the exteriorization step, end piece 23 may be located anywhere inside the lumen of the vessel. For example, end piece 23 may appose the vessel wall. For example, end piece 23 may appose the vessel wall at a location roughly diametrically opposed to the puncture site. For example, end-piece 23 may partially or completely penetrate the vessel wall. For example, end-piece 23 may completely penetrate the vessel wall. For example, proximal end piece 22 may be located outside the lumen of the vessel, across the lumen of the vessel, or inside the lumen of the vessel. End piece 22 may comprise an anchor configured to prevent the migration of device 22 by securing it to the tissue of the vessel wall, or to tissue proximate the vessel wall.

In some embodiments, system 70 may cause device 20 to rotate, bend, or twist in order to prevent the build-up of torsion during device exteriorization. In some embodiments, system 70 may cause device 20 to rotate, bend, or twist in order to release torsion accumulated in the device.

Figure 8:
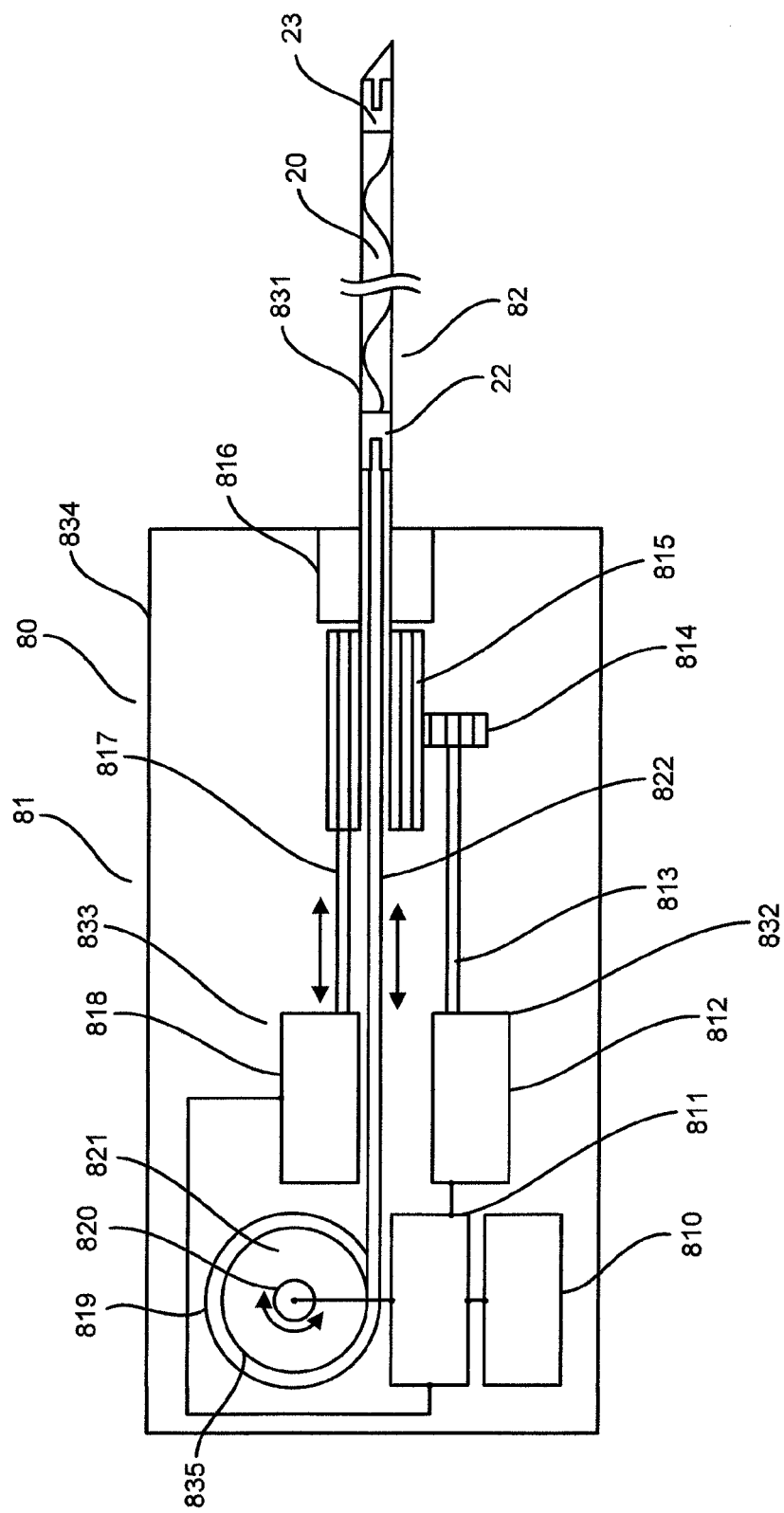
FIG. 8 is a schematic representation of an automatic system according to some embodiments of the present disclosure, which is intended for implanting a monofilament filtering device (or any other monofilament device) according to some embodiments of the present disclosure.

Reference is now made to FIG. 8, which schematically represents some embodiments of a system 80 for providing embolic protection. System 80 comprises a patient-external unit 81 and a patient-internal unit 82. Patient external unit 81 may be disposable or reusable. Patient-internal unit 82 may be disposable. Device 80 may be sterilizable using means known in the art, such as ETO sterilization, gamma ray sterilization, and their likes. Patient-internal unit 82 may reversibly connect and disconnect from patient-external unit 81 whenever unit 81 is reusable. Such reversible connection means may comprise any known reversible connections means such as, for example, a screw.

Patient-external unit 81 may comprise a power supply 810, a control unit 811, driving mechanisms 819, 832, and 833, gear ring 815, and bearing 816, all of which may be housed in housing 834. Patient-internal unit 82 may comprise needle 831 and filtering device 20. Filtering device 20 may reside in its undeployed, substantially linear state within the lumen of needle 831.

Power supply 810 and control unit 811 may be substantially similar to power supply 71 and control unit 72, respectively. Therefore, their detailed description is omitted here.

Driving mechanism 833 may configured to advance or retract needle 831 with respect to housing 834. Driving mechanism 832 is configured to rotate needle 831. Driving mechanism 819 is configured to advance or retract device 20 with respect to housing 834. Bearing 816 is configured to allow needle 831 to rotate with respect to housing 834. Gear ring 815 may be configured to couple needle 831 to driving mechanisms 832 and 833. Gear ring 815 may attach to the proximal end of needle 831 around the circumference of needle 831.

Driving mechanism 833 may comprise a motor 818 and a shaft 817. Motor 818 may be substantially similar to the one or more motors comprised in one or more driving mechanism 73. Therefore, a detailed description of motor 818 is omitted here. Shaft 817 may be configured to transmit the linear (advancement/retraction) motion generated by motor 818 to gear ring 815, thereby advancing or retracting gear wheel 815 (and needle 831 to which gear wheel 815 may be rigidly connected) with respect to housing 834.

Gear wheel 815 may be connected to shaft 817 in the following way: gear wheel 815 may comprise a circular groove (not shown) at its proximal end, and the tip of shaft 817 may be inserted in this groove. The shape of the groove may be made such that its opening to the proximal face of gear wheel 815 may be narrower than its interior. Similarly shaft 817 may comprise a bulb at its distal tip, whose maximal width is larger than the size of the opening of the groove. Thus, whenever the tip of shaft 817 is inserted in the groove, linear motion of shaft 817 is translated to likewise linear motion of gear wheel 815 (and needle 831) by the coupling between the shaft and the groove. However, gear wheel 815 is free to rotate without hindrance from shaft 817 because the tip of shaft 817 is free to slide within the channel of the groove.

Driving mechanism 832 may comprise a motor 812, a shaft 813, and a gear wheel 814. Motor 812 may be substantially similar to the one or more of the motors comprised in one or more driving mechanism 73. Therefore, a detailed description of motor 812 is omitted here. Shaft 832 is configured to transmit the rotary motion generated by motor 812 to gear wheel 814.

Gear ring 815 and gear wheel 814 may be connected by means of interlocking gear teeth. Therefore, the rotation of gear wheel 814 is translated to rotation of gear ring 815. Because gear ring 815 is rigidly connected to needle 831, rotation of gear wheel 814 translates to rotation of needle 831.

Gear wheel 814 may be configured to slide with respect to gear ring 815 in the linear (advancement/retraction) direction. In this way, rotational coupling between gear wheel 814 and gear ring 815 is preserved regardless of the linear position of bear ring 815 (and needle 831). Needle 831 may be free to rotate with respect to housing 834 by means of bearing 816.

Driving mechanism 819 may comprise a motor 835 and a push wire 822. Motor 835, which may be of any of the types comprised by one or more driving mechanism 73, may comprise a stator 820 and a rotor 821. The proximal portion of flexible push wire 822 may be rolled around rotor 821. The distal end of push wire 822, which may reside in the lumen of needle 831, may be coupled to the proximal end of device 20. The coupling may be reversible. For example, disconnection of the coupling may be realized using mechanical or electrical means as known in the art, such as, electrolysis.

Whenever motor 835 is configured to cause rotor 821 to rotate in the counterclockwise direction, push wire 822 may then advance relative to needle 831, and device 20 caused to advance relative to the needle. Whenever motor 835 is made to cause rotor 821 to rotate in the clockwise direction, push wire 822 is retracted with respect to needle 831. This may or may not cause device 20 to also retract with respect to the needle, depending on the type of coupling between push wire 822 and the proximal part of device 20.

Figure 9B:
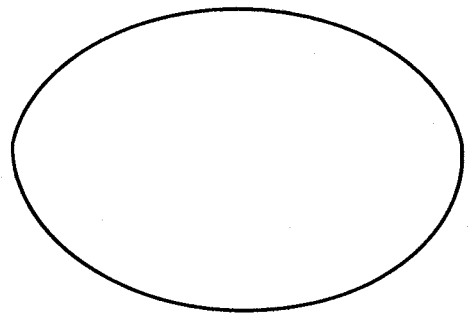
FIG. 9B depicts a perpendicular cross section of an end-piece of a filtering device (or any other monofilament device) according to the present disclosure.
Figure 9A:
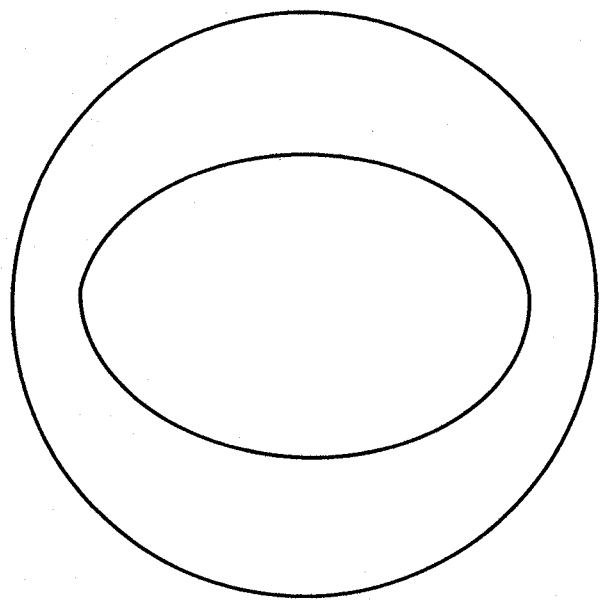
FIG. 9A depicts a perpendicular cross section of a needle of an automatic system of some embodiments of the present disclosure.

Whenever needle 831 rotates with respect to housing 834, the rotational motion is transmitted to device 20. The transmission of rotational motion between the needle and the device may be realized by friction between the interior walls of the needle and the device. Alternatively, the inner cross-section of the needle may have a noncircular shape (FIG. 9A), and one or more of the end-pieces 22 and 23 may have a perpendicular cross-sectional shape that interlocks with the cross sectional shape of the needle lumen (FIG. 9B).

In operation, power supply 810 provides electrical or mechanical power to control unit 811. Control unit 811 transmits power and/or signals to driving mechanisms 832, 833, and 81 according to a predetermined program stored in the control unit, or by instructions from the operator that are transmitted to the control unit via its man machine interface. Any combination of linear and/or rotational motions of needle 831 and/or device 20 with respect to external housing 834 may be implemented.

In some embodiments, the implantation of filtering device 20 by means of automatic system 80 in a body vessel may proceed as follows. First, a physician determines that it is desirable to implant filtering device 20 in the body vessel. Under the guidance of a suitable imaging modality (not shown), such as, for example, ultrasound, high resolution ultrasound, or CT scanning, or without imaging guidance at all, the operator punctures the skin adjacent to the vessel using the sharp end of needle 831. The operator then carefully advances system 80 through the subcutaneous tissue, and transversely punctures the vessel at approximately diametrically-opposed sites. The sharp end of needle 831 may then be advanced a few more millimeters interiorly into the patient, so that end piece 23 is exterior to the lumen of the vessel. Once this positioning is achieved, the operator instructs control unit 811 to execute a predetermined program (which optionally depends on inputs from one or more sensor), which causes device 20 to be properly exteriorized, such that the end pieces are external to the vessel lumen and the filament of device 20 is properly arranged within the lumen. Once the device 20 is properly exteriorized, the operator extracts system 80 from the patient's body.

In some embodiments, the implantation of filtering device 20 by means of automatic system 80 in a body vessel may proceed as in the previous paragraph until the step in which the operator punctures the body vessel. Instead of making two substantially diametrically-opposed punctures in the vessel wall, the operator makes a single puncture in the vessel wall using needle 831, or using distal end-piece 23, which may comprise a sharp tip. The operator the places the distal tip of needle 831, or the distal tip of end-piece 23, in the lumen of the vessel. The operator then instructs control unit 810 to execute a predetermined program (which optionally depends on inputs from one or more sensor), which causes device 20 to be properly exteriorized. Upon the completion of the exteriorization step, end piece 23 may be located anywhere inside the lumen of the vessel. For example, end piece 23 may appose the vessel wall. For example, end piece 23 may appose the vessel wall at a location roughly diametrically opposed to the puncture site. For example, end-piece 23 may partially or completely penetrate the vessel wall. For example, end-piece 23 may completely penetrate the vessel wall. For example, proximal end piece 22 may be located outside the lumen of the vessel, across the lumen of the vessel, or inside the lumen of the vessel. Typically, end piece 22 may comprise an anchor configured to prevent the migration of device 22 by securing it to the tissue of the vessel wall, or to tissue proximate the vessel wall.

In some embodiments, system 80 may cause device 20 to rotate, bend, or twist in order to prevent the build-up of torsion during device exteriorization. In some embodiments, system 80 may cause device 20 to rotate, bend, or twist in order to release torsion accumulated in the device.

In some embodiments, a system similar to 80 is feasible, in which the needle does not rotate but device 20 is free to rotate within the needle. Such a delivery device need not have a bearing 816 and a driving mechanism 832. Instead, a different driving mechanism is configured to rotate device 20 inside the lumen of needle 831 by rotating pusher 822 inside the needle and rotationally coupling the pusher to device 20.

Systems 70 and/or 80 may be used to deliver all monofilament implants that have a substantially linear undeployed state and a bent and/or twisted deployed state. Such devices, including vessel occluders, stents, drug delivery platforms, radiation delivery platforms, PFO occluders, Left Atrial Appendage Occluders, and their likes, are described in Provisional Patent Application 61/708,273 to Yodfat and Shinar, which is incorporated herein by reference. All monofilament device embodiments described in 61/653,676 and also in Provisional Patent Applications 61/693,979 and 61/746,423 to Shinar and Yodfat, may possess end-pieces such as 22 and 23 of the present Provisional Application.

Reference is now made to FIGS. 10A and 10B, which depict a side view and a cross-sectional view of device 20 in operation. Device 20 is implanted in body vessel 80 such that its north-south axis is substantially perpendicular to the principal axis of symmetry of vessel 80. Embolus 81 may be filtered by device 20 because the spacing 6 between consecutive windings of the device is smaller than the size of the embolus. The embolus may thus filter by size exclusion.

It is understood that monofilament filtering devices according to some embodiments of the present disclosure are possible in which, in the deployed state, each end of the filament may either reside inside the lumen of a body vessel, in the wall of the vessel, or exteriorly to the wall of the vessel. For example, a device in which the proximal end resides entirely within the lumen and the distal end resides exteriorly to the vessel is possible. A device in which both ends reside in the vessel wall without penetrating the vessel's exterior wall is possible. In this way, for each end all different combinations of penetration depths (in-lumen, in-wall, exterior to wall) are possible.

It is understood that monofilament filtering devices according to some embodiments of the present disclosure are possible in which, in the deployed state, the proximal end of the monofilament extends exteriorly from the patient's skin, or is implanted subcutaneously immediately below the patient's skin. Such devices are particularly suited for temporary usage, in which it is desired to retrieve the device shortly after a temporary embolus-enticing cause, such as surgery or minimally-invasive procedure, is removed.

Although the embodiments of the present disclosure have been herein shown and described in what is conceived to be the most practical way, it is recognized that departures can be made from one and/or another of the disclosed embodiments and are within the scope of the present disclosure, which is not to be limited to the details described herein. The following exemplary claims aid in illustrating an exemplary scope of at least some of the embodiments disclosed herein.

We claim:

1. A monofilament filtering device (MFD) implantation system for implanting a MFD within a human blood vessel comprising:
    an MFD;
    a housing;
    a power supply;
    a control unit;
    at least one of a geared driving mechanism and a motorized driving mechanism;
    and
    a needle comprising a hollow lumen, a proximal end, and a distal end, wherein the needle is configured to receive the MFD in an undeployed state,
    wherein
        the MFD is configured for both an undeployed and a deployed state after implantation within a blood vessel including a helical portion,
        the MFD is exteriorized from the needle by the operation of the driving mechanism, and
        after implantation, at least the helical portion is within the blood vessel.

2. The system of claim 1, wherein the driving mechanism is configured to rotate, bend, or twist the MFD.

3. The system of claim 1, wherein the driving mechanism is configured to advance or retract the MFD.

4. The system of claim 1, wherein the driving mechanism is configured to advance or retract the needle.

5. The system of claim 1, further comprising one or more sensors.

6. The system of claim 5, wherein the at least one sensor is mounted on the needle.

7. The system of claim 5, wherein the at least one sensor comprises a pressure sensor.

8. The system of claim 1, wherein the housing, the power supply, the control unit, and the driving mechanism reside in a patient-external unit.

9. The system of claim 8, wherein the patient-external unit is disposable.

10. The system of claim 8, wherein the patient-external unit is reusable.

11. The system of claim 8, wherein the needle and the MFD comprise a patient-internal unit.

12. The system of claim 11, wherein the patient-external unit and the patient-internal unit are reversibly connected.

13. The system of claim 1, wherein the power supply is electrical and/or mechanical.

14. The system of claim 1, wherein the power supply is a direct current source or an alternating current source.

15. The system of claim 1, wherein the control unit comprises one or more of: an interface, an input/output device, an analog or digital electronic controller, and a computer processor.

16. The system of claim 1, further comprising at least one of a pusher and a rotor.

17. The system of claim 16, wherein the driving mechanism is configured to move at least one of the pusher, the needle and the MFD so as deploy the MFD into the vessel.

18. The system of claim 16, wherein the pusher configured to push or otherwise move at least the MFD relative to the needle.

* * * * *